(12) United States Patent
Paschal

(10) Patent No.: US 11,779,249 B2
(45) Date of Patent: Oct. 10, 2023

(54) MAGNETIC LANCET DEVICE

(71) Applicant: DYNAMIC MAGNETICS, LLC, Franklin, TN (US)

(72) Inventor: Richard C. Paschal, Nashville, TN (US)

(73) Assignee: DYNAMIC MAGNETICS, LLC, Franklin, TN (US)

( * ) Notice: Subject to any disclaimer, the term of this patent is extended or adjusted under 35 U.S.C. 154(b) by 0 days.

(21) Appl. No.: 17/878,560

(22) Filed: Aug. 1, 2022

(65) Prior Publication Data

US 2022/0361785 A1 Nov. 17, 2022

Related U.S. Application Data

(63) Continuation of application No. 16/544,374, filed on Aug. 19, 2019, now abandoned, which is a continuation of application No. 15/615,424, filed on Jun. 6, 2017, now Pat. No. 10,383,560, which is a continuation of application No. 14/975,164, filed on Dec. 18, 2015, now Pat. No. 9,700,254, which is a continuation of application No. 11/837,153, filed on Aug. 10, 2007, now Pat. No. 9,247,898.

(51) Int. Cl.
*A61B 5/151* (2006.01)
*A61B 5/15* (2006.01)
*A61B 17/3209* (2006.01)

(52) U.S. Cl.
CPC ........ *A61B 5/15123* (2013.01); *A61B 5/1411* (2013.01); *A61B 5/1513* (2013.01); *A61B 5/15019* (2013.01); *A61B 5/1519* (2013.01); *A61B 5/150022* (2013.01); *A61B 5/15113* (2013.01); *A61B 5/15194* (2013.01); *A61B 5/150198* (2013.01); *A61B 5/150412* (2013.01); *A61B 5/150519* (2013.01); *A61B 5/150717* (2013.01); *A61B 17/32093* (2013.01)

(58) Field of Classification Search
CPC ............ A61B 5/1411; A61B 5/150022; A61B 5/150412; A61B 5/150717; A61B 5/15113; A61B 5/1513; A61B 5/1519; A61B 5/15194; A61B 17/32093
See application file for complete search history.

(56) References Cited

U.S. PATENT DOCUMENTS

| 4,054,944 | A  | * | 10/1977 | Lau ........................ H01H 5/02 200/530 |
| 7,015,782 | B2 | * | 3/2006  | Kincaid .................. F04B 9/02 335/207 |
| 7,666,053 | B2 | * | 2/2010  | O'Keefe ................ A63H 17/26 206/758 |
| 2009/0306695 | A1 | * | 12/2009 | Brenneman ...... A61B 5/150503 606/181 |

* cited by examiner

Primary Examiner — Sarah A Long
(74) Attorney, Agent, or Firm — K&L Gates LLP; Shu Chen

(57) ABSTRACT

Embodiments of the present invention provide magnetic lancet devices and methods for driving a lancet. For example, a magnetic lancet device may include a driving mechanism having a plurality of magnets and a lancet coupled to the driving mechanism. A magnetic interaction between the plurality of magnets is configured to drive the lancet from an engaged position to a penetrating position.

16 Claims, 10 Drawing Sheets

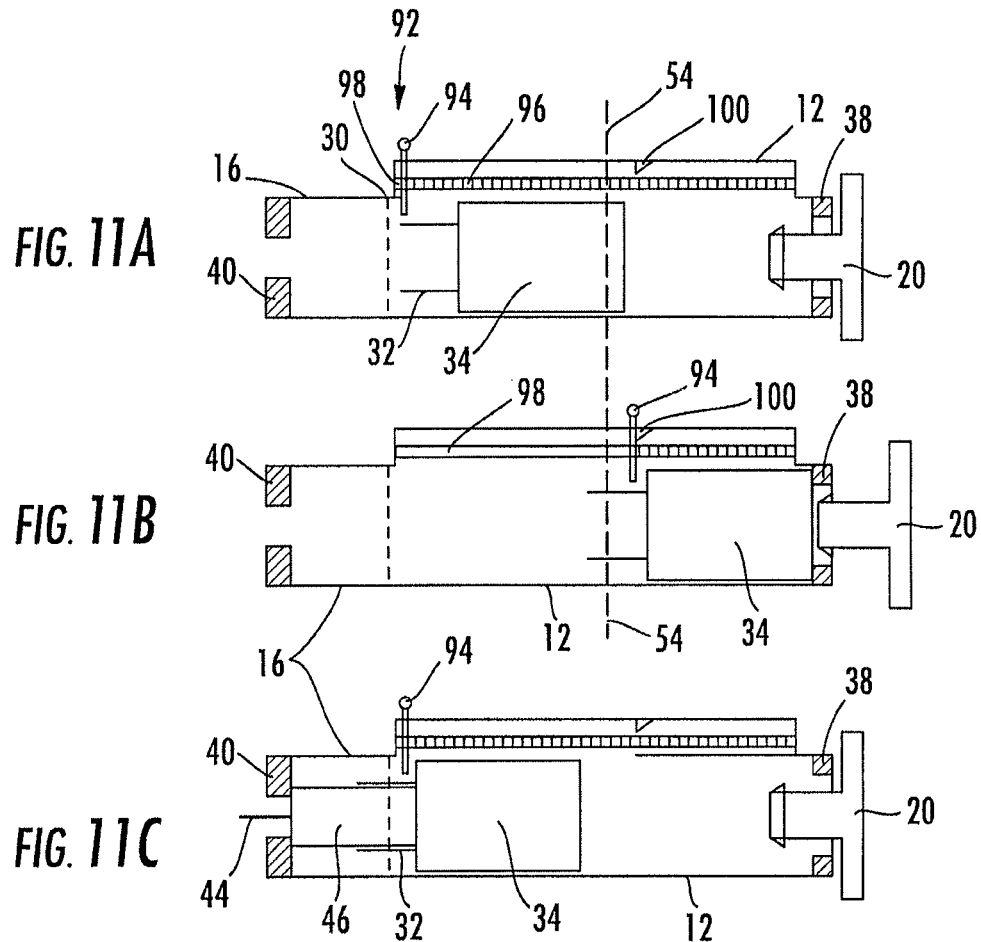

MAGNETIC LANCET DEVICE

CROSS REFERENCE TO RELATED APPLICATIONS

This application is a continuation of U.S. patent application Ser. No. 16/544,374, filed Aug. 19, 2019, which is a continuation of U.S. patent application Ser. No. 15/615,424, filed Jun. 6, 2017, now patented as U.S. Pat. No. 10,383,560, which is a continuation of U.S. patent application Ser. No. 14/975,164, filed Dec. 18, 2015, now patented as U.S. Pat. No. 9,700,254, which is a continuation of U.S. patent application Ser. No. 11/837,153, filed Aug. 10, 2007, now patented as U.S. Pat. No. 9,247,898, which are incorporated by reference herein in their entirety.

FIELD OF THE INVENTION

Embodiments of the present invention relate generally to lancet devices and, more particularly, to a lancet device utilizing a magnet driving mechanism.

BACKGROUND OF THE INVENTION

A major objective in educating patients on how to deal with the disease of diabetes is to have them recognize the importance of regularly checking their blood glucose levels. Currently, blood glucose testing meters have advanced to a level requiring a very small blood sample; however, obtaining even a small sample with a lancet device still inflicts unpredictable discomfort that many patients refuse to tolerate. In reality, the initial function of all reusable lancet devices begins to degrade from the first use and gradually tissue penetration depth varies even though the depth settings on the devices remain unchanged. Many lancet device designs involve some form of elastic mechanism (e.g., a metal spring) that compresses under stress (in an engaged or a cocked position) and returns to a relaxed state when the stress is removed (decompression after release). With repeated use (compression and decompression of the elastic material) there is a gradual change from the initial elasticity design of the drive mechanism. This change may adversely affect the functional design parameters of a lancet device and result in inconsistent lancet tissue penetration depth. Depth settings may become unreliable and deviations in the speed of entry and withdrawal of lancets into tissue may occur. Such changes may lead directly to user discomfort. A newly diagnosed diabetic patient may initially find blood glucose testing acceptable but later discover that the depth setting on his lancet device (e.g., a setting of level 4 on a 1 through 9 depth scale) suddenly or gradually changes to a greater or lesser tissue penetration depth. Patients often attempt to offset these changes by adjusting their lancet devices to compensate for this unexpected development. Once the patients determine a new acceptable depth setting, which frequently involves pain resulting from trial and error, the elasticity of the drive mechanism may again change. Understandably, this scenario results in patient frustration and reluctance to continue glucose testing.

Drive mechanisms employing magnetic forces have been developed. For example, electromagnet drive mechanisms have been developed but may be impractical for home or away-from-home glucose testing. In addition, U.S. Patent Application Publication No. 2005/0125019 to Kudrna et al. discloses a lancet device comprising an internal magnet for driving and retracting a lancet. An outer sleeve is attached to a collar, while the magnet and lancet are secured to an inner sleeve. The inner sleeve is capable of moving longitudinally within the outer sleeve. Kudrna also discloses an arming member for moving the lancet, collar, and inner and outer sleeves to an armed position. A button switch activates the device such that the attractive force between the magnet and the collar propels the lancet forward to a piercing position. In addition, Kudrna discloses that the attractive force between the magnet and the collar acts to retract the lancet to a steady-state position.

Despite these improvements in lancet devices, it would be advantageous to provide a lancet device that provides reliable and consistent depth penetration. Moreover, it would be advantageous to provide a lancet device that is easily manufactured and user friendly. In addition, it would be advantageous to provide a lancet device that is inexpensive and of simple construction.

SUMMARY OF THE INVENTION

Embodiments of the present invention provide magnetic lancet devices and methods for driving a lancet. In general, the magnetic lancet device includes a driving mechanism having a plurality of magnets that interact with one another to drive a lancet from an engaged position to a piercing position. For example, the lancet may be coupled to a carrier magnet that is displaceable within a guide tube, wherein the carrier magnet is configured to interact with one or more magnets coupled to the guide tube.

According to one embodiment of the present invention, a magnetic lancet device is provided. The magnetic lancet device includes a driving mechanism comprising a plurality of magnets and a lancet coupled to the driving mechanism. A magnetic interaction between the magnets is configured to drive the lancet from an engaged position to a penetrating position. The magnetic interaction may also be configured to withdraw the lancet from the penetrating position to a disengaged position. In addition, the magnetic interaction may be attractive for maintaining the lancet in the disengaged position, while the magnetic interaction may be a magnetic repulsive interaction for maintaining the lancet in the engaged position, and/or driving the lancet from the engaged position to the penetrating position.

According to various aspects of the magnetic lancet device, at least one of the magnets is coupled to a guide tube, and at least one of the magnets is a carrier magnet coupled to the lancet and positioned within the guide tube. A magnetic interaction between the magnet of the guide tube and the carrier magnet is configured to drive the lancet from the engaged position to the penetrating position. The guide tube may include a pair of magnets with like poles positioned opposite one another and generally perpendicular to a longitudinal axis of the guide tube. Furthermore, the driving mechanism may include a longitudinal driving member coupled to the carrier magnet. The driving member may include an adjustment mechanism at its proximal end that is threadably adjustable and configured to adjust a depth of penetration of the lancet in the penetrating position. The guide tube may include one or more stops configured to abut the carrier magnet in the engaged position and/or abut the adjustment mechanism in the penetrating position.

Further aspects of the magnetic lancet device include a guide tube having an adjustable and removable end cap coupled to a distal end thereof, wherein the end cap comprises a stop configured to stop the lancet at a predetermined penetrating position. The lancet device may further include a magnetic stop positioned proximate to a distal end of the guide tube, wherein a magnetic repulse interaction between the carrier magnet and the magnet stop is configured to stop the lancet at a predetermined penetrating position such that the carrier magnet and magnetic stop do not physically contact one another. Moreover, the lancet may include a magnetic insert configured to attract to the carrier magnet so as to secure the lancet to the carrier magnet. The lancet device may also include a mechanism configured to move the lancet from a disengaged position to the engaged position.

An additional embodiment of the present invention provides a magnetic lancet device that includes a carrier magnet and a lancet comprising a magnetic insert. A magnetic interaction between the carrier magnet and the magnetic insert is configured to couple the lancet to the carrier magnet. The lancet may be coupled to a distal end of the carrier magnet. The lancet device may further include a guide tube comprising at least one magnet, wherein the carrier magnet is positioned within the guide tube such that a magnetic repulse interaction between the at least one magnet of the guide tube and the carrier magnet is configured to drive the lancet from an engaged position to a penetrating position.

Another embodiment of the present invention provides a magnetic lancet device. The lancet device includes a guide tube comprising at least one magnetic stop and a carrier magnet positioned within the guide tube. The lancet device also includes a lancet coupled to the carrier magnet, wherein a magnetic repulse interaction between the carrier magnet and the magnet stop is configured to stop the lancet at a predetermined penetrating position such that the carrier magnet and magnetic stop do not physically contact one another. According to one aspect of the lancet device, the guide tube includes a pair of magnets positioned opposite one another and generally perpendicular to a longitudinal axis of the guide tube. The lancet device may also include a longitudinal driving member, wherein the carrier magnet is coupled to a proximal end of the driving member, and the lancet is coupled to a distal end of the driving member.

A further aspect of the present invention provides a method for driving a lancet with a driving mechanism. The method includes positioning the lancet in an engaged position and driving the lancet to a penetrating position in response to a magnetic interaction between a plurality of magnets associated with the driving mechanism. The positioning step could include withdrawing the lancet from a disengaged position to the engaged position, while the driving step may include biasing the lancet such that the lancet is propelled in response to a magnetic repulse interaction between the plurality of magnets. The positioning step could also include biasing the lancet such that the lancet is maintained in the engaged position in response to a magnetic repulse interaction between the plurality of magnets. The method may also include coupling the lancet to one of the magnets with a magnetic insert associated with the lancet. Additionally, the method may include adjusting a depth of penetration of the lancet.

Therefore, embodiments of the present invention may provide several advantages. For example, the magnetic lancet device may reduce many of the problems associated with prior art that result in patient frustration and reluctance to test their blood glucose. Additionally, the magnetic lancet device may have an increased functional life, and the magnetic field strength of the drive mechanism may never change. The tissue penetration depth settings may also not change assuming the lancet and lancet housing morphology is constant, and lancet oscillation at the point of tissue contact may be reduced. Moreover, the magnetic lancet device may be used with existing lancet designs or use a lancet according to one embodiment of the present invention, wherein the lancet incorporates a magnet for stabilizing the lancet in a fixed position to the drive mechanism. The guide tube of the lancet device may provide better control of a lancet in its forward motion toward tissue contact resulting in reduced lateral motion and associated discomfort during tissue penetration and withdrawal. Furthermore, used lancets may be easily removed from the drive mechanism for disposal. In addition, the magnetic drive mechanism of the invention may endure direct impact into barrier stops with limited or no degradation. Embodiments of the present invention do not require electrical current (ac or dc) enabling a patient to use the device at any location regardless of the availability of electricity or batteries.

BRIEF DESCRIPTION OF THE DRAWINGS

Figure 1:
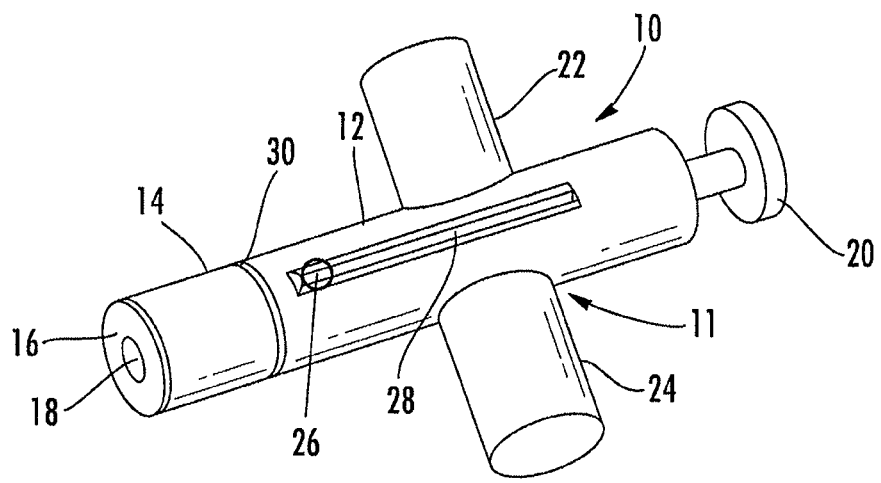
Figure 2:
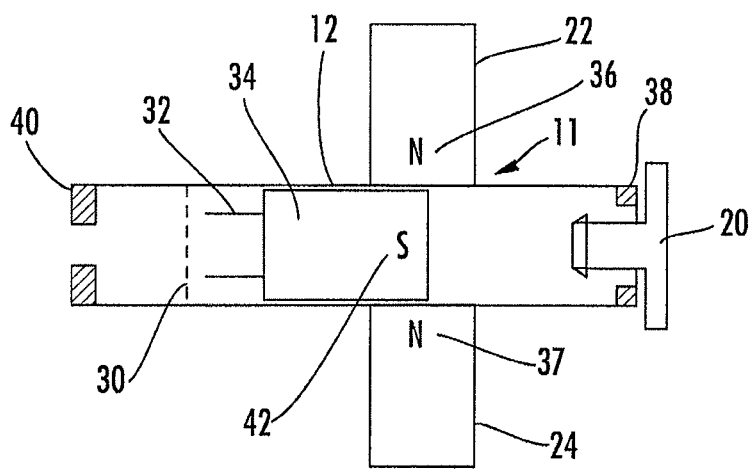
Figure 3:
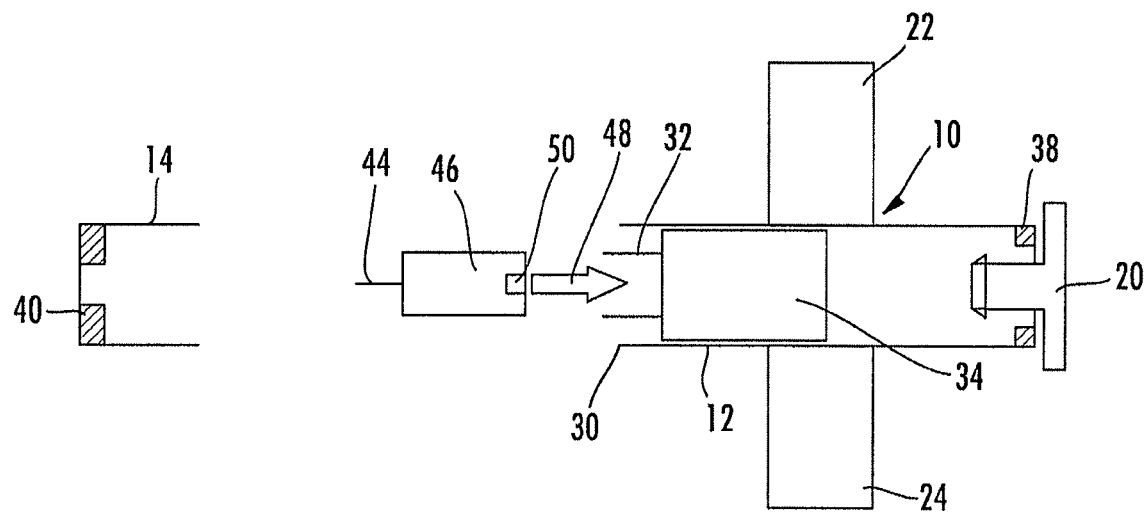
Figure 4:
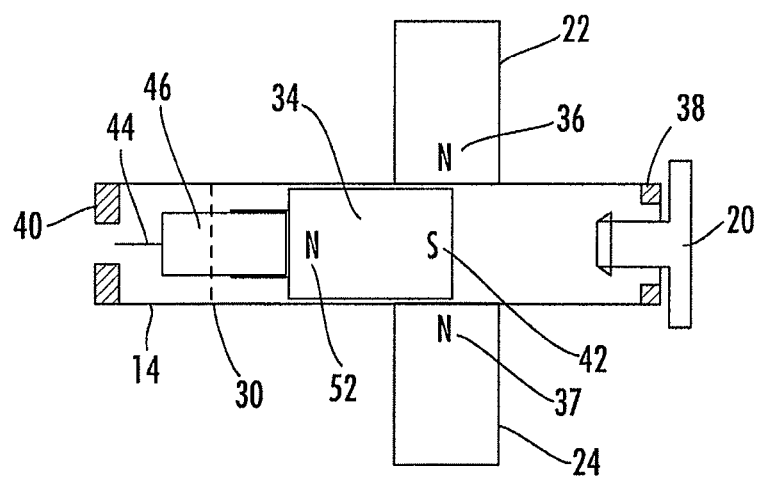
Figure 5:
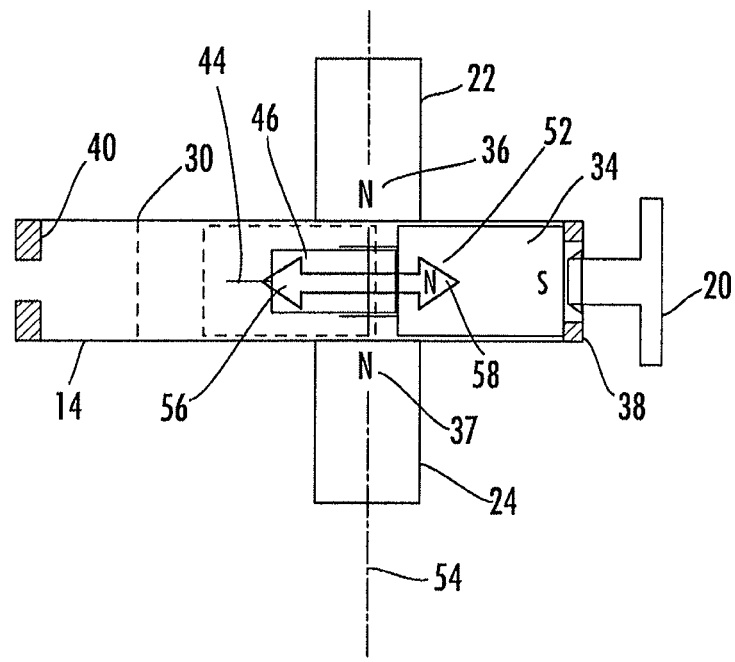
Figure 6:
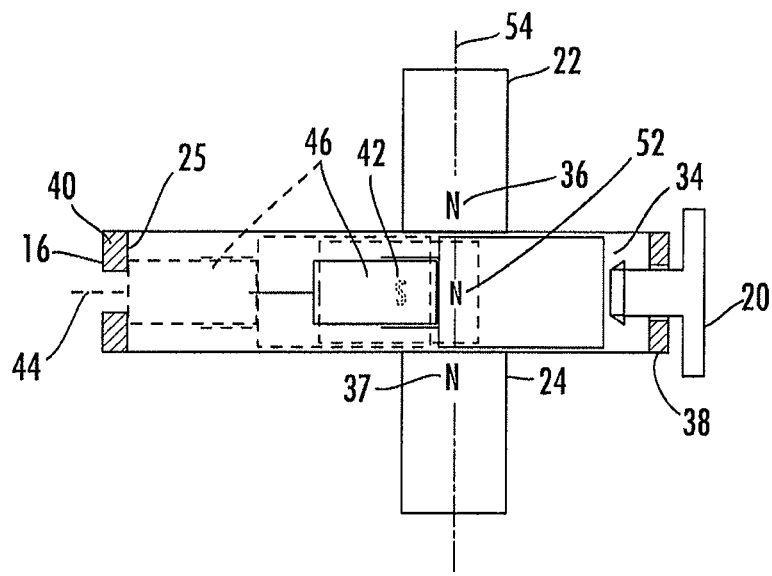
Figure 7:
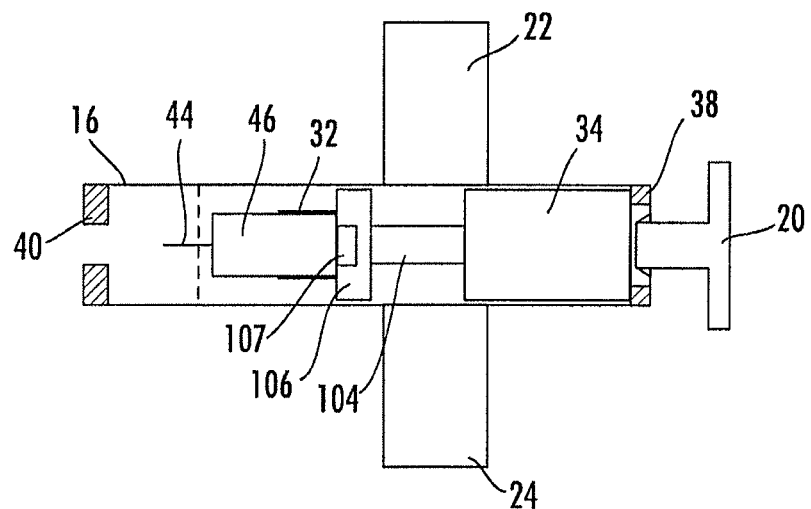
Figure 8:
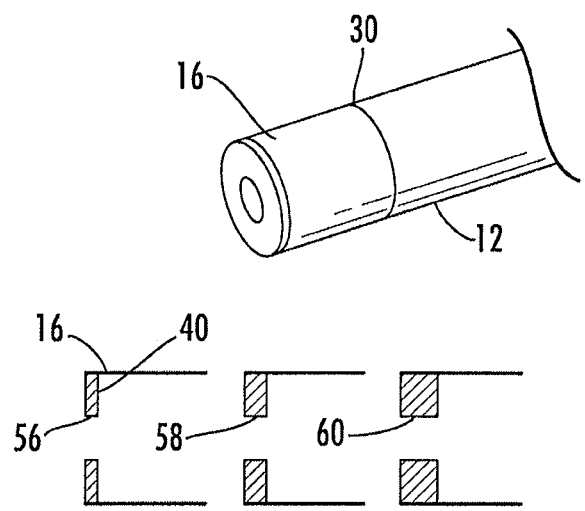
Figure 9:
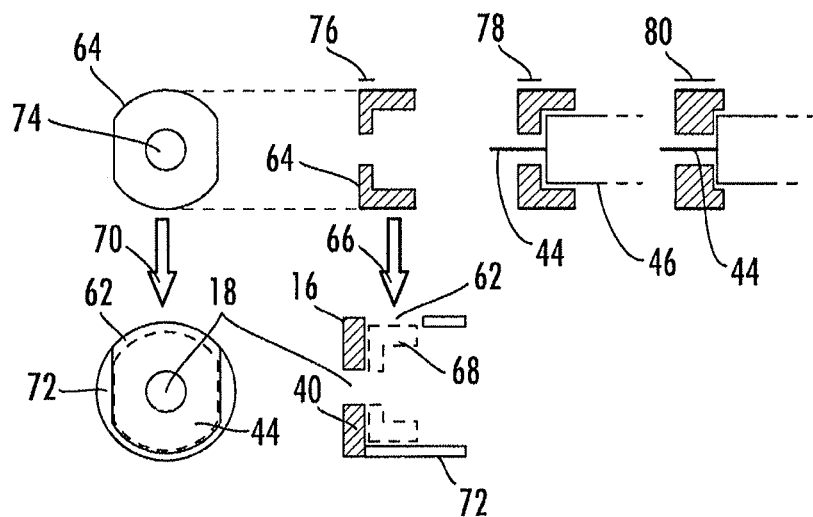
Figure 10:
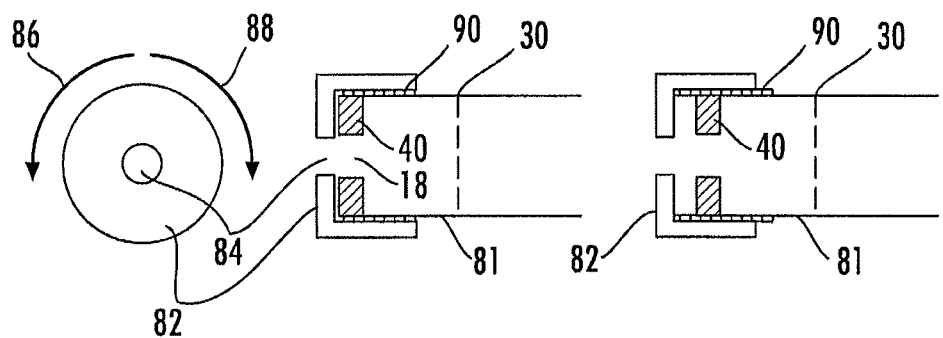
Figure 12A:
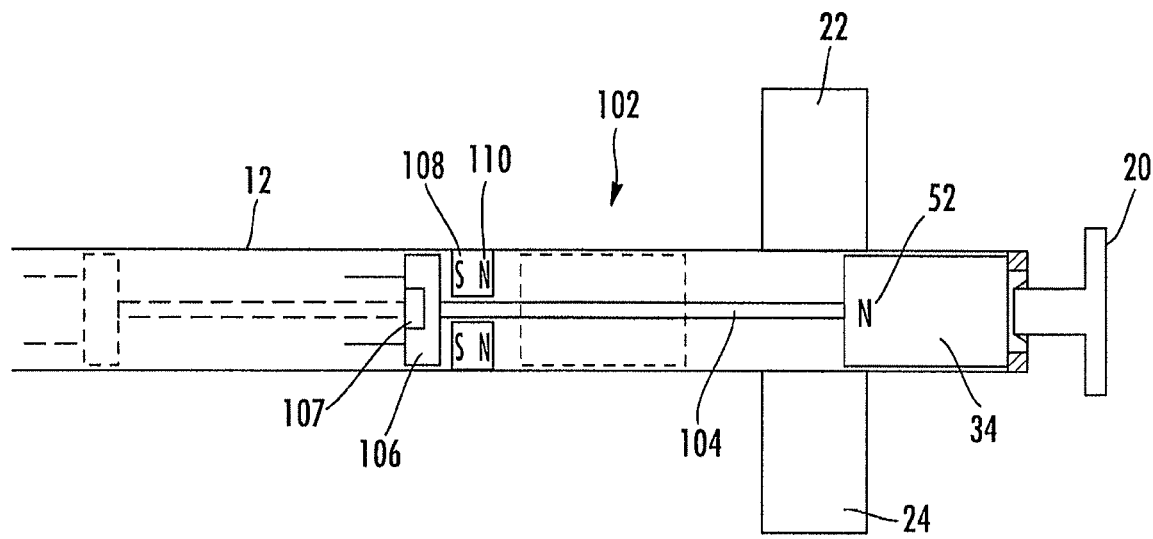
Figure 12B:
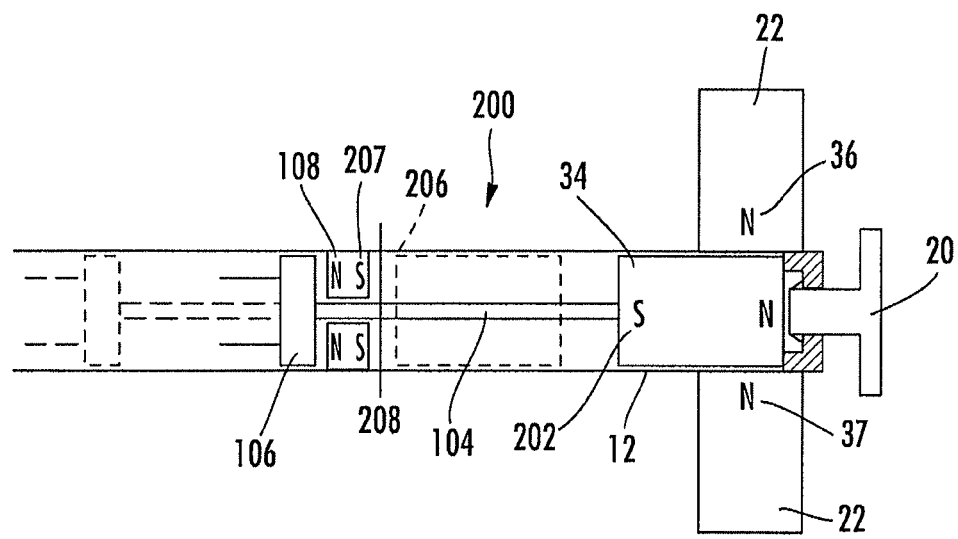
Figure 13:
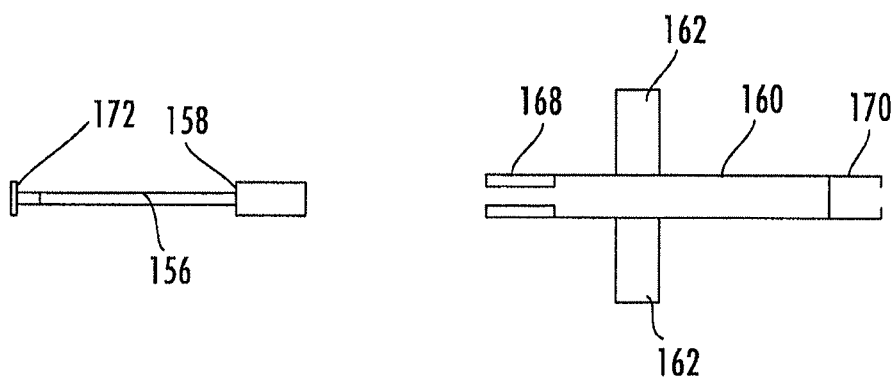
Figure 14:
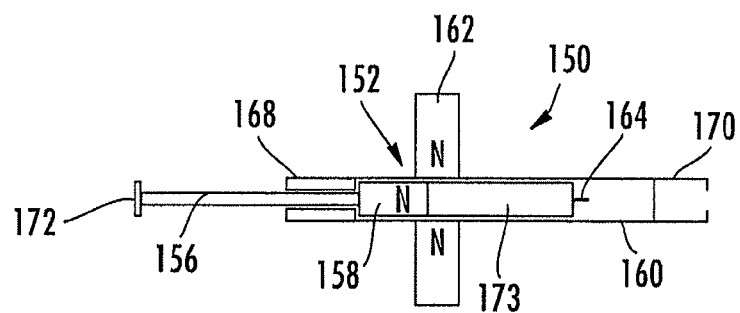
Figure 15:
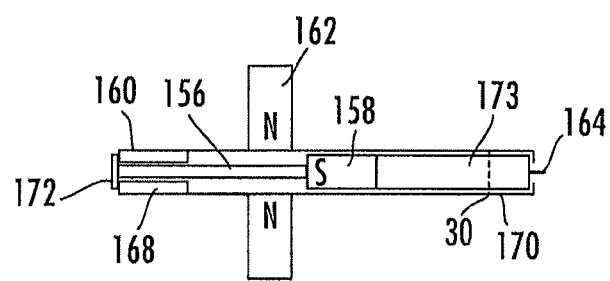
Figure 16:
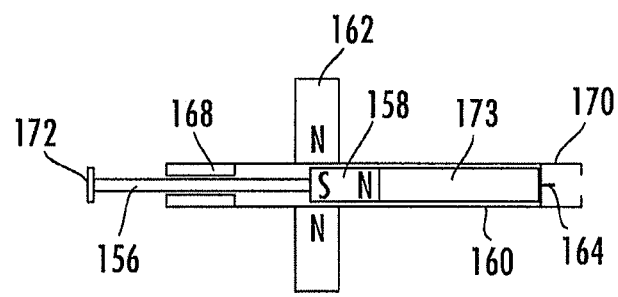
Figure 17:
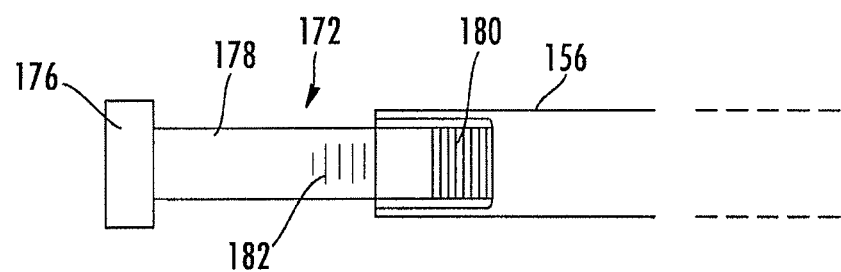

Having thus described various embodiments of the invention in general terms, reference will now be made to the accompanying drawings, which are not necessarily drawn to scale, and wherein:

FIG. 1 shows a perspective view of a magnetic lancet device according to one embodiment of the present invention;

FIG. 2 illustrates a cross-sectional view of the magnetic lancet device of FIG. 1;

FIG. 3 depicts a cross-sectional view of the insertion of a lancet into the magnetic lancet device of FIG. 1;

FIG. 4 shows a cross-sectional view of the magnetic lancet device of FIG. 1 with the lancet inserted therein and in a disengaged position;

FIG. 5 illustrates a cross-sectional view of the magnet lancet device of FIG. 1 with the lancet in an engaged position;

FIG. 6 depicts a cross-sectional view of the magnet lancet device of FIG. 1 with the lancet in a driving position and penetrating position;

FIG. 7 shows a cross-sectional view of a magnetic lancet device according to a further embodiment of the present invention;

FIG. 8 shows a perspective view of an end cap and cross-sectional views of the end cap according to one embodiment of the present invention;

FIG. 9 shows an end view of an end cap and cross-sectional views of the end cap according to another embodiment of the present invention;

FIG. 10 illustrates an end view of an end cap and cross-sectional views of the end cap according to an additional embodiment of the present invention;

FIGS. 11A-C depicts cross-sectional views of a cocking mechanism according to one embodiment of the present invention; and FIG. 12A shows a cross-sectional view of a magnetic lancet device according to an additional embodiment of the present invention;

FIG. 12B shows a cross-sectional view of a magnetic lancet device according to one embodiment of the present invention;

FIG. 13 illustrates a cross-sectional view of an unassembled magnetic lancet device including a driving mechanism according to one embodiment of the present invention;

FIG. 14 depicts the magnetic lancet device of FIG. 13 with the driving mechanism assembled and in an engaged position;

FIG. 15 shows the magnetic lancet device of FIG. 13 in a penetrating position;

FIG. 16 shows the magnetic lancet device of FIG. 13 in a disengaged position; and FIG. 17 depicts an adjustment mechanism according to one embodiment of the present invention.

DETAILED DESCRIPTION

The present inventions now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Referring to FIGS. 1-6, there is shown a magnetic lancet device 10 according to one embodiment of the present invention. The lancet device 10 generally includes a driving mechanism 11 comprising a plurality of magnets that are configured to interact with one another to drive a lancet 44. In particular, the lancet device 10 is capable of driving the lancet 44 to a penetrating position and withdrawing the lancet from the penetrating position. Thus, the lancet device 10 is capable of driving the lancet 44 to a consistent penetrating position such that user fear and frustration may be reduced. In addition, the lancet device 10 includes limited moving parts such that the lancet device may be easily assembled and inexpensive.

It is understood that the magnetic lancet device 10 is capable of being used to obtain a small sample of blood for a variety of applications. For example, the lancet device 10 may be used for diabetic patients to check blood glucose levels. In addition, driving mechanism 11 of the lancet device 10 may be used in conjunction with other applications for driving an object other than a lancet 44, including but not limited to, toys, sporting goods, or any other application where a conventional spring driving mechanism is used to propel an object.

FIG. 1 shows a magnetic lancet device 10 according to one embodiment of the present invention. The lancet device 10 includes a driving mechanism 11, which comprises a plurality of magnets. The lancet device 10 includes a hollow nonmagnetic guide tube 12 having a release button 20 coupled to its proximal end and a removable end cap 14 coupled to its distal end. The guide tube 12 can be separated at joint 30 allowing the end cap 14 to be detached for insertion of a lancet 44. An engagement (cocking) lever 26 passes through slot 28 defined in the guide tube 12, which enables an operator to prime or cock the driving mechanism prior to each use (i.e., move the lancet from the disengaged position to the engaged position). The end cap 14 has a flat tissue contact surface 16 and an aperture 18 through which a lancet 44 may extend and retract when the driving mechanism 11 is engaged and the release button 20 is depressed.

As shown in FIG. 1, the driving mechanism 11 includes a pair of driving or external magnets 22 and 24 having a longitudinal axis that is aligned generally perpendicular to the longitudinal axis of the guide tube 12. FIG. 2 illustrates that the external magnets 22 and 24 are affixed to guide tube 12 with their North poles 36, 37 stabilized in repulse positions (i.e., proximate to one another). FIG. 2 also shows that the driving mechanism 11 includes a carrier magnet 34 that is housed within the guide tube 12, wherein the outer diameter of the carrier magnet is slightly less than the internal diameter of the guide tube 12 such that the carrier magnet can move longitudinally within the guide tube between a proximal stop 38 and a distal stop 40. The South pole 42 of the carrier magnet 34 is stabilized between the North poles 36, 37 of the external magnets 22, 24. In the configuration shown in FIG. 2, the carrier magnet 34 is in a disengaged position. In the disengaged position, the magnetic attraction force fields interacting between the magnets 22, 24, 34 stabilize the carrier magnet 34 in a fixed position, i.e., no force is present to cause proximal or distal movement of the carrier magnet 34 within the guide tube 12.

FIG. 3 shows that the carrier magnet 34 includes a cradle 32 for receiving a lancet 44 therein. In particular, the cradle 32 is accessible for insertion of the lancet housing 46 when the end cap 14 of the guide tube 12 is detached at separation joint 30. The lancet 44 and lancet housing 46 are inserted into the lancet cradle 32 as shown by directional arrow 48. The lancet housing 46 may be equipped with a magnetic insert 50 positioned at its proximal end and coupled to the carrier magnet 34 via magnetic attractive forces. In comparison to conventional metal inserts, the magnetic insert 50 may improve the stabilization of the lancet 44 and lancet housing 46 against the carrier magnet 34 and prevent slippage therebetween. The magnetic insert 50 could be of various sizes and in various positions within the lancet housing 46. Other lancets not including a magnet insert 50 may be employed with the lancet device 10 according to additional embodiments of the present invention, such as a traditional lancet that may be press fit with the lancet cradle 32.

FIG. 4 shows the end cap 14 reattached at joint 30 with magnet 34, lancet 44, and lancet housing 46 in the disengaged position within the guide tube 12. As stated above, in the disengaged position, the South pole 42 of the carrier magnet 34 is stabilized in a fixed position between the North pole 36 of magnet 22 and North pole 37 of magnet 24. However, when the engagement lever 26 is moved proximally through slot 28, a force is applied to the carrier magnet 34 such that the carrier magnet is moved proximally to an engaged position and secured against stop 38, as shown in FIG. 5. The movement of carrier magnet 34 from the disengaged position to the engaged position by engagement lever 26 positions the North poles 36, 37, 52 of magnets 22, 24, 34, respectively, in a magnetic repulse field, which maintains the lancet in the engaged position. Line 54 denotes the point at which the repulse magnetic field shifts between a repulsive force for maintaining the lancet 44 in the engaged position and a repulsive force for driving the lancet to the penetrating position as North pole 52 passes between North pole 36 and North pole 37. In FIG. 5, the repulse magnetic fields on the distal and proximal sides of line 54 are indicated by arrow 56 and arrow 58 respectively.

As described above, a force is required by an operator to push the engagement lever 26 and, thus, the carrier magnet 34 from the disengaged position to the engaged position. At the instant the North pole 52 of the carrier magnet 34 is pushed beyond line 54, the carrier magnet is caught in a repulse field in the proximal direction (shown by arrow 58) and propelled into stop 38. Stop 38 terminates the movement of the carrier magnet 34 short of clearing the repulse field indicated by arrow 58. In the engaged position, the North pole 52 of the carrier magnet 34 is located proximate to line 54 such that a small force in the distal direction results in the North pole 52 crossing back over line 54 and into the repulse field indicated by arrow 56. The repulse field indicated by arrow 56 acts as the driving force required to drive the lancet 44 from the engaged position to the penetrating position. Thus, in response to a distal force, the carrier magnet 34 is accelerated in the distal direction until the lancet carrier 46 collides with the anterior stop 40, as shown in dashed lines in FIG. 6. The stops 38, 40 may be various materials such as a rigid material, or a flexible material to enhance bounce (e.g., elastic, rubber, etc.). Moreover, there may be a magnetic material positioned proximate to the aperture 18 that may enhance the return of the lancet 44 to the disengaged position.

Referring again to FIG. 5, when the North pole 52 of the carrier magnet 34 is moved to the engaged position to rest against stop 38, the magnetic driving mechanism 11 is primed (cocked) and ready for release. Lancet release button 20 is extended to become the release means (trigger) for pushing the North pole 52 of the carrier magnet 34 distally beyond line 54 so as to propel the lancet 44 to the penetrating position (shown in dotted lines in FIG. 6). FIG. 6 illustrates the release button 20 depressed and consequently repositioning the North pole 52 of the carrier magnet 34 distally to pass line 54. At the point the carrier magnet 34 is thrust forward to the penetrating position represented by dotted lines, the distal movement is terminated by the collision of the lancet housing 46 with stop 40. The collision and termination of distal movement results in a return of the carrier magnet 34 in the proximal direction to the disengaged position, as shown in FIG. 4. The proximal movement of the carrier magnet 34, lancet housing 46, and lancet 44 results from the magnetic attractive interaction between the North pole 36 of magnet 22, North pole 37 of magnet 24, and the South pole 42 of the carrier magnet 34.

FIG. 6 demonstrates that tissue penetration depth of the lancet 44 in the penetrating position is related to the location where the lancet housing 46 impacts the stop 40. Assuming that the lancet 44 and lancet housing 46 morphology remain a constant, the tissue penetration depth may be regulated by the thickness of the stop 40.

According to one aspect of the present invention, the end cap 16 may include various thicknesses of stops 40 such that the ends may be interchanged to vary the depth of penetration. For example, the end cap 16 may include a stop 40 having a thickness of 3 mm, and the lancet 44 may have a length of 10 mm. Thus, the lancet 44 is prevented from extending more than 7 mm distally out of the end cap 16.

FIG. 8 illustrates three optional techniques for accomplishing tissue penetration depth accuracy. In particular, FIG. 8 shows three alternate designs of end caps 16 detached from the guide tube 12 at joint 30. The stop 40 may have various wall thicknesses, such as thicknesses 56, 58, 60 measuring 2 mm, 4 mm, and 6 mm, respectively. Each stop 40 would provide different limits to the distance a lancet 44 could extend distally beyond the end cap 16 to penetrate tissue. In this particular embodiment, a variety of end caps 16 could be supplied with a lancet device 10 each with an imprinted depth marking. A patient could test the end caps 16 with the least penetration depth and move up to what the patient considered the end cap that was most acceptable. The patient could then store the other end caps 16 for potential adjustment if needed.

According to an additional aspect of the present invention, FIG. 9 shows that an end cap 72 may be configured with a slot 62 to receive and house a depth limiting disk 64. Arrow 66 depicts the insertion path of disk 64 into slot 62 with dotted lines 68 representing the seated position of the disk 64 within end cap 72. Arrow 70 depicts an end view of the end cap 72 along the same insertion path as arrow 66, wherein the end cap 72 receives and stabilizes disk 64 within slot 62 so that disk aperture 74 is in alignment with end cap aperture 18. The disk 64 could include a pin or similar mechanism to facilitate insertion within and removal of the disk from the slot 62.

The thickness of the disk 64 may be varied to change the depth of penetration of the lancet 44 in the penetrating position. For instance, FIG. 9 shows that the disk 64 may be configured with three different depth thicknesses 76, 78, 80, which correspond, for example, to 3 mm, 4 mm, and 6 mm thicknesses, respectively. Thus, the extension of a 10 mm lancet 44 beyond the distal end of the end cap 72 would be 3 mm where the thickness 78 of the disk 64 is 4 mm (including a stop 40 of 3 mm in thickness), and an extension of 1 mm for a disk having thickness 80 of 6 mm (including a stop 40 of 3 mm in thickness).

FIG. 10 depicts another embodiment of the present invention for a lancet depth regulating mechanism. The end cap 81 includes an external threaded surface which engages an internal threaded surface of a screw-on member 82. An aperture 84 is defined in the cap 82 that is capable of aligning with the aperture 18 of the end cap 81. The screw-on member 82 can be rotated in a counterclockwise direction (indicated by arrow 86) to increase the space between the screw-on member 82 and the distal end of the end cap 81 (e.g., from 1 mm to 4 mm). Conversely, the distance between the screw-on member 82 and the end cap 81 may be decreased by rotating the screw-on member 82 in a clockwise direction (indicated by arrow 88). The interlocking threads 90 of the screw-on member 82 and end cap 81 may be varied to enable a wide range of rotation and different positions in order to obtain a desired depth of penetration of the lancet 44. A depth level scale (not shown) could be imprinted on the exterior surface of the screw-on member 82 and/or the end cap 81 in order to obtain a desired depth of penetration, and a locking mechanism (not shown) could enable a patient to lock the screw-on member 82 and end cap 81 at a desired depth level.

FIGS. 11A-C illustrate an engagement mechanism 92 according to one embodiment of the present invention. In particular, FIG. 11A shows that the engagement mechanism 92 includes an engagement lever 94 in a rest position at the distal end of a fully extended spring 96 within a spring encasement channel 98. In FIG. 11A, the carrier magnet 34 is in the disengaged position. The distal end of engagement (cocking) lever 94 extends inwardly within the guide tube 12 such that moving the lever 94 proximally engages a distal end of the carrier magnet 34. In FIG. 11B the engagement lever 94 has been moved proximally to fully compress the spring 96 within the encasement channel 98. As such, the distal end of the lever 94 is configured to carry the carrier magnet 34 within the guide tube 12 proximally of the line 54 to the engaged position. Proximal movement of the lever 94 is limited by a stop 100 extending within the guide tube 12. FIG. 11C depicts the carrier magnet 34 in the penetrating position, wherein the lancet 44 is at the limit of its distal movement.

FIGS. 7 and 12A illustrate an additional aspect of the driving mechanism. In particular, FIG. 7 shows that a spacing bar 104 extends between the carrier magnet 34 and a lancet cradle 106. FIG. 12A depicts a lancet device 102 that similarly includes a longitudinal spacing bar 104 that extends between a distal end of the carrier magnet 34 and a proximal end of a lancet cradle 106. The spacing bar 104 may be attached to the carrier magnet 34 and lancet cradle 106 via nonmagnetic or magnetic techniques. The lancet cradle 106 may include a magnetic insert 107 that facilitates coupling with a magnetic insert 50 associated with the lancet housing 46.

FIG. 12A illustrates a lancet device 102 according to an additional embodiment of the present invention. More specifically, FIG. 12A illustrates that the guide tube 12 includes a magnet stop 108 that is capable of stopping the lancet 44 in a predetermined penetrating position (shown in dashed lines). The magnetic stop 108 may be attached internally or externally of the guide tube 12. A magnetic repulsive interaction between a North pole 110 of the magnetic stop 108 and the North pole 52 of the carrier magnet 34 may be employed to stop the lancet 44. Thus, the carrier magnet 34 may stop short of physically contacting the magnetic stop 108. Consequently, the functional life of the lancet device 102 may be increased by reducing wear resulting from physical contact between the carrier magnet 34 and a stop.

FIG. 12B illustrates an additional embodiment of a lancet device 200. The lancet device 200 is similar to that shown in FIG. 12A, however, external magnets 22 have been moved proximally on the guide tube 12, and the polarity of the carrier magnet 34 has been reversed such that the South pole 202 of the carrier magnet is more remote from the North poles 36, 37 of the external magnets. In addition, the polarity of the magnet stop 108 has been reversed such that the magnetic repulse field between the South pole 207 of the magnetic stop and the South pole 202 of the carrier magnet 34 is employed to stop the lancet 44 in a predetermined penetrating position without the carrier magnet physically contacting the magnetic stop. The movement of the carrier magnet 34 from the penetrating position to the disengaged position may result from compression of the magnetic repulse field between the South pole 202 of the carrier magnet and the South pole 207 of the magnetic stop 108. The compression of the magnetic repulse field distally beyond line 208 may result in movement of the carrier magnet 34 beyond the stabilization or disengaged position 206 of the carrier magnet such that the magnetic repulse field causes proximal movement of the carrier magnet beyond line 208 and the carrier magnet is withdrawn to the disengaged position.

Referring to FIGS. 13-17, a lancet device 150 according to another embodiment of the present invention is shown. The lancet device 150 includes a driving mechanism 152 that includes a driving member 156 coupled to a carrier magnet 158 at its distal end. An adjustable end cap 172 is coupled to a proximal end of the driving member 156 for adjusting the depth of a lancet 164 in the penetrating position, as will be explained in further detail below. A lancet 164 is coupled to the distal end of the carrier magnet 158. The lancet 164 may include a lancet housing 173 that couples to the carrier magnet 158 via magnetic attraction.

The driving mechanism 152 also includes a guide tube 160 having a pair of magnets 162 positioned opposite from one another. As before, the longitudinal axis of the pair of magnets 162 are positioned generally perpendicular to the longitudinal axis of the guide tube 160. As shown in FIG. 14, the guide tube 160 is configured to receive the driving member 156 and carrier magnet 158 therein, and the driving member and carrier magnet are capable of sliding proximally and distally within the guide tube. FIG. 13 illustrates that the guide tube 160 includes a stop 168 at its proximal end and a removable end cap 170 at its distal end.

As described above, the interaction of the magnets 158, 162 may be configured to propel the lancet 164 into tissue and then pull the lancet out of tissue. More specifically, FIG. 14 illustrates the lancet 164 in an engaged position, wherein the magnetic repulse field between the magnets 158, 162 maintains the lancet in the engaged or driving position absent any mechanical locking mechanisms. As shown in FIG. 14, the North poles of the magnets 162 are positioned adjacent to the guide tube 160, and the North pole of the carrier magnet 158 is positioned proximate to the magnets 162, which results in a magnetic repulse field that maintains the lancet 164 in the engaged position.

Motion of the lancet from the engaged position to the penetrating position may be initiated by a user pushing on the adjustable end cap 172 in a distal direction. By applying a force on the end cap 172 in the distal direction, the magnetic repulse field between the carrier magnet 158 and magnets 162 maintaining the lancet 164 in the engaged position may be overcome and shifted such that the lancet 164 is propelled via magnetic interaction to the penetrating position. FIG. 15 illustrates the lancet 164 in a penetrating position, wherein the lancet extends distally out of the end cap 170 to penetrate tissue. The distance that the lancet 164 protrudes from the end cap 170 may be limited by physical contact between the lancet housing 173 and the end cap 170. Moreover, FIG. 16 depicts the lancet 164 in a disengaged position, wherein the lancet is retracted from the penetrating position in response to the magnetic attraction between the North poles of the magnets 162 and the South pole of the carrier magnet 158. The user may then pull the adjustable end cap 172 in a proximal direction in order to position the lancet 164 in the engaged position.

The lancet device 150 may include an adjustable end cap 172. FIG. 17 depicts an adjustable end cap 172 according to one embodiment of the present invention. The end cap 172 is configured to adjust a depth of the lancet 164 in the penetrating position. In particular, FIG. 15 shows the end cap 172 contacting the proximal end of the guide tube 160 such that the depth of the lancet 164 in the penetrating position is limited. The end cap 172 includes a knob 176, and a shaft 178 that is in telescoping engagement with the driving member 156. The shaft 178 may include external threads 180 that engage with internal threads defined within the driving member 156. Thus, the distance that the knob 176 extends from the proximal end of the driving member 156 may be adjusted by rotating the knob in a clockwise or counterclockwise direction. The shaft 178 could include a scale 182 that is imprinted thereon such that the user may adjust the depth of the lancet 164 in the penetrating position to a predetermined distance (i.e., the distance between the knob 176 and the stop 168).

It is understood that the magnetic lancet devices 10, 102, 150 described herein are not meant to be limiting, as various sizes, configurations, and modifications of the lancet devices may be employed in additional aspects of the present invention, and different features may be interchangeable with one another. For instance, the engagement mechanism 92 shown in FIG. 11 could be employed with the lancet device 150. In addition, the lancet devices may include various techniques to position the lancet in the engaging position, stop the lancet at a desired depth in the penetrating position, and activate the lancet for driving from the engaged position. Moreover, the guide tube, end cap, and magnets may be various sizes and configurations that enable a lancet to be driven into and out of tissue via a driving mechanism including a plurality of magnets. For instance, although a pair of magnets are shown affixed to a guide tube, one or more magnets may be employed, wherein the magnets may be natural or manmade neodymium magnets. In addition, the driving or external magnets may be positioned internally within the guide tube rather than externally of the guide tube as shown. The user could also use the external magnets as grips when activating the lancet device, such as by wrapping the user's index and middle finger around the magnets and activating the release button with the user's thumb. In addition, the location of the magnetic poles is for illustrative purposes only, as the poles may be varied or reversed, and the size and shape of the magnets need not be cylindrical. Moreover, the angular orientation and flux angles of the magnets could be changed to adjust the repulse/attractive forces in either direction.

The lancet devices may also include various features in addition to that shown in the drawings. For example, the lancet devices may include air vents to prevent potential positive or negative pressure within the guide tube distally of the carrier magnet as the carrier magnet is propelled distally. The lancet devices may be various materials such as a polymeric material. Furthermore, the lancet devices may be reusable such that only the used lancets may be disposed of. For instance, the end cap could be removed, and the used lancet could be driven into a disposable device for sanitary disposal. In addition, the opposite end of the disposable device could include a new lancet such that the new lancet may be easily inserted into the lancet device. The lancets discussed herein, such as those incorporating a magnetic insert, could also be used with conventional lancet devices.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A device, comprising:
   a guide tube including a driving end and a lancet end and having a longitudinal axis extending between the driving end and the lancet end;
   a first magnet and a second magnet positioned on opposite sides along a length of the guide tube with like poles facing each other, the first and second magnets having magnetic axes extending between their north and south poles, the magnetic axes being generally perpendicular to the longitudinal axis of the guide tube;
   a driving member having a first distal end coupled to a third magnet that is positioned within the guide tube and a second proximal end coupled to a first end cap, wherein the third magnet is configured to maintain in an engaged position with a first pole being disposed proximate to the magnetic axes of the first and second magnets, the first pole being identical to the like poles of the first and second magnets; and
   a lancet coupled to an end of the third magnet disposed towards the lancet end,
   wherein, in response to a force applied to the first end cap, the driving member is configured to propel the third magnet and the lancet from the engaged position to a penetrating position protruding from the lancet end of the guide tube.

2. The device of claim 1, wherein a second pole of the third magnet is attracted by the like poles of the first and second magnet to withdraw the lancet from the penetrating position to a disengaged position.

3. The device of claim 2, further comprising a lancet housing with a first end coupled to the lancet and a second end coupled to the third magnet.

4. The device of claim 3, further comprising a second end cap implemented on the lancet end of the guide tube.

5. The device of claim 4, wherein the second end cap is configured to be detachable from the guide tube at a joint, the second end cap includes at least one stop configured to regulate a tissue penetration depth of the lancet, and the at least one stop is configured to have various wall thicknesses.

6. The device of claim 5, wherein the second end cap is configured to indicate a penetration depth marking relating to a wall thickness of the at least one stop.

7. The device of claim 4, wherein the second end cap is configured to receive and house a disk that is detachable from the second end cap.

8. The device of claim 7, wherein the disk is configured to have various depth thicknesses for regulating a tissue penetration depth of the lancet.

9. The device of claim 4, wherein the second end cap includes an external threaded surface configured to engage an internal threaded surface of a screw-on member.

10. The device of claim 9, wherein a distance between the screw-on member and the second end cap is varied by rotating the screw-on member relative to the second end cap.

11. The device of claim 10, wherein an exterior surface of the screw-on member is configured to have a depth level scale imprinted thereon to indicate a depth of penetration of the lancet.

12. The device of claim 1, wherein the first end cap is configured to include a knob and a shaft that is in a telescoping engagement with the driving member.

13. The device of claim 12, wherein the shaft is configured to include external threads that engage with internal threads of the driving member.

14. The device of claim 12, wherein a distance that the knob extends from the second proximal end of the driving member is adjusted by rotating the knob in a clockwise or counterclockwise direction.

15. The device of claim 12, wherein the shaft is configured to include a scale imprinted thereon to indicate a depth of penetration of the lancet.

16. The device of claim 1, further comprising one or more air vents to prevent positive or negative pressure within the guide tube.

* * * * *